United States Patent [19]

Pagnotta et al.

[11] Patent Number: 5,449,808
[45] Date of Patent: Sep. 12, 1995

[54] METHOD FOR CONVERTING AMIDES TO NITRILES AND NITRILES TO AMIDES

[75] Inventors: Marco Pagnotta, Edison, N.J.; Mark C. Cesa, South Euclid, Ohio; Sandra L. Denman, Brunswick, Ohio; Robert D. Boyer, Jr., Macedonia, Ohio

[73] Assignee: The Standard Oil Company, Cleveland, Ohio

[21] Appl. No.: 283,252

[22] Filed: Mar. 29, 1994

Related U.S. Application Data

[63] Continuation of Ser. No. 758,192, Sep. 11, 1991, abandoned, which is a continuation of Ser. No. 238,660, Aug. 31, 1988, abandoned.

[51] Int. Cl.$^6$ .................... C07C 253/30; C07C 231/12
[52] U.S. Cl. ....................... 558/357; 558/370; 558/371; 558/378; 564/124; 564/125; 564/130; 564/131; 564/137
[58] Field of Search ............... 558/378, 357; 564/124, 564/125, 130, 131, 137

[56] References Cited

U.S. PATENT DOCUMENTS 2,461,842  2/1949  Olin ..................... 558/445
4,851,546  7/1989  Graham et al. ............ 548/543

OTHER PUBLICATIONS

Kirk-Othmer, *Encyclopedia of Chemical Technology*, Third Edition, vol. 5, John Wiley & Sons, New York, (1979), pp. 16–55.

Vinokurov, et al., Journal of Organic Chemistry, U.S.S.R., vol. 23, No. 8, Part 2 (Jan. 20, 1988), p. 1602.

*Primary Examiner*—Joseph Paul Brust
*Attorney, Agent, or Firm*—Michael F. Esposito; David P. Yusko; David J. Untener

[57] ABSTRACT

A process which comprises contacting and catalytically reacting under essentially anhydrous conditions in the liquid phase an amide with a nitrile according to the equation:

$$RCONH_2 + R^1CN \rightleftharpoons RCN + R^1CONH_2$$

where R and $R^1$ are not the same and are each selected from (1) H, hydrocarbyl, a hydrocarbyl group substituted with: one or more of F, Cl, Br, I, amido, cyano, formyl, hydrocarbylcarbonyl, hydrocarbyloxy, hydrocarbyloxycarbonyl, hydrocarbylcarbonyloxy and dihydrocarbylamino, and (2) any of group (1) where one or more H atoms are substituted by a deuterium atom.

1 Claim, No Drawings

METHOD FOR CONVERTING AMIDES TO NITRILES AND NITRILES TO AMIDES

This is a continuation of application of Ser. No. 07/758,192 filed Sep. 11, 1991 which is a continuation of application Ser. No. 238,660 filed Aug. 31, 1988, both now abandoned.

This invention concerns a new reaction, viz., the anhydrous reaction of a first nitrile with a first amide to make a second nitrile and a second amide.

Thus, according to the present invention there is provided a process which comprises contacting and reacting under essentially anhydrous conditions in the liquid phase an amide with a nitrile according to the equation:

$$RCONH_2 + R^1CN \rightleftharpoons RCN + R^1CONH_2$$

where R and $R^1$ are not the same and are each selected from (1) H, hydrocarbyl, and a hydrocarbyl group substituted with: one or more of F, Cl, Br, I, amido, cyano, formyl, hydrocarbylcarbonyl, hydrocarbyloxy, hydrocarbyloxycarbonyl, hydrocarbylcarbonyloxy and dihydrocarbylamino, and (2) any of group (1) where one or more H atoms are substituted by a deuterium atom.

In the process of the present invention, HCN is considered to be a nitrile.

We regard the foregoing essentially anhydrous reaction per se as our invention since it is a completely new and unreported reaction. We have found that the reaction does not proceed to a detectable degree in the absence of a catalyst. We have found that the Pt and Pd catalysts discussed herein, including those shown in the specific examples, promote the new reaction, and there are no doubt other catalysts as yet untried that will be effective. However, since we have discovered an unexpected, unreported new reaction we regard the scope of our invention to be the anhydrous catalytic reaction of an amide with a nitrile according to the foregoing equation, divorced from any designation of a specific catalyst.

In the Journal of Organic Chemistry of the USSR, Vol. 23, No. 8 Part 2, nominal publication date Jan. 20, 1988, Plenum Publishing Corporation, New York, N.Y. (English translation of the earlier Russian article), there is disclosed a dehydration-hydration reaction whereby acetonitrile is reacted with, for instance, hexanamide or benzamide, and sulfuric acid, to make acetamide and hexanenitrile and hexanoic acid; or to make acetamide, benzonitrile and benzoic acid, respectively. This reaction is a hydration of the acetonitrile by water in the sulfuric acid, hydrolysis of the substrate amide by water in the sulfuric acid and a dehydration of the substrate amide to supply water to the sulfuric acid.

On the other hand, the present reaction is a transfer of the elements of water from the amide to the nitrile, a completely new reaction, accomplished under anhydrous conditions, and without formation of any carboxylic acid.

Catalysts that are useful in the present process include those with the formula $$M_mX_aL_b$$

where M is selected from Pd and Pt, X contains zero to 10 C atoms, is selected from halogen, H, O, —CO, acyloxy, trihaloacetyloxy, hydroxy, dialkylamino, thio, thioacyl, nitro, tetraalkylboron and tetraalkylaluminum; where m is 1 or 2, a is zero, 2 or 4; when m is 1 and a is zero, b is 2, 3 or 4; when m is 1 and a is 2, b is zero or an integer from 1 to 4; when m is 1 and a is 4, b is 4 or 6; when m is 2, a+b are a total of 6;

where L has the formula $TR^2_n$, where T is selected from B, N, P, Bi, Al, As, Sb, Li, Na, K, Rb and Cs; each $R^2$ is the same or different, contains zero to 10 C atoms and is independently selected from H, halogen, nitro, trihalomethyl, acyl, acyloxy, acylthio, hydrocarbyl, hydrocarbyloxy and dihydrocarbylamino; and if T is alkali metal, n is zero; if T is not alkali metal, n is 3 or 4;

with the proviso that the reaction mixture can optionally additionally contain as a catalyst modifier a compound $ZR^2_c$ where Z is selected from B, N, P, Bi, Al, As and Sb; $R^2$ is as before defined and c is a number selected to satisfy the valance requirements of Z.

Now preferred catalysts are compounds $$MX_a$$

where M is a before defined, X is halogen and a is 2.

The reaction of the present invention is usually effected at temperatures in the range from 20° C. to 250° C., although higher or lower temperatures can be used, and the optimum temperature for a given reaction can be determined by routine experimentation.

In our process R and $R^1$ usually contain from zero to 15 C atoms, although the process is fully applicable when R and $R^1$ contain more than 15 C atoms.

As will be seen in the specific examples, solvents can be used to facilitate the reaction. Such solvents can include, for instance, non-reactive solvents such as ethers, glymes, THF and dioxane. In an appropriate case, the solvent can be a liquid organic nitrile or organic amine, which can be, or can include, an excess of one of the reactants.

Moreover, as will be understood, if one wishes to maximize the conversion of the nitrile reactant to an amide, one can accomplish this for instance, by using a high molar ratio of amide reactant to nitrile reactant. Similarly, one way to maximize formation of the desired nitrile is to use a high ratio of the nitrile reactant in excess of the amide reactant.

Other obvious methods include maximizing the nitrile product by continuously removing the product nitrile as it is formed.

It has also been found that the reaction is accelerated by including in the reaction mixture a non-reactive, sterically hindered, non-nucleophilic base such as di-tert-butylpyridine, triisopropylamine, and quinuclidine.

The following specific examples illustrate this invention but are not to be considered limiting:

Example 1

A solution of acetamide (1.4502 g, 24.55 mmol), 4-bromobenzonitrile (0.7818 g, 4.79 mmol), PdBr$_2$ (66.5 mg, 0.25 mmol) and durene (63.7 mg, 0.4746 mmol, internal standard) in 25 mL of 2-methoxyethyl ether (diglyme) was heated with stirring to reflux for 24 hours. The conversion of 4-bromobenzonitrile was 24% and 4-bromobenzamide was identified by GC-MS as the only amide product. Acetonitrile was also formed.

Example 2

A solution of acetamide (1.4876 g, 25.19 mmol), 1,4-dicyanobenzene (0.4349 g, 3.39 mmol), PdBr$_2$ (58.0 mg, 0.217 mmol), and durene (46.4 mg, 0.346 mmol) in 25 mL of diglyme was stirred at reflux for 45 hours. The conversion of 1,4-dicyanobenzene was 40%, and 4-cyanobenzamide was identified by GC-MS as the only amide product. Acetonitrile was also formed.

Example 3

A solution of acetamide (1.3758 g, 23.29 mmol), 4-cyanobenzaldehyde (0.5067 g, 3.86 mmol), PdBr$_2$ (73.3 mg, 0.275 mmol), and durene (81.6 mg, 0.608 mmol) in 25 mL of diglyme was stirred at reflux for 48 hours. The conversion of 4-cyanobenzaldehyde was 58%, and 4-formylbenzamide was identified by GC-MS in the product mixture. Acetonitrile is also formed.

Example 4

A solution of acetamide (1.3435 g, 22.7 mmol), methyl 4-cyanobenzoate (0.6104 g, 3.79 mmol), PdBr$_2$ (69.4 mg, 0.2607 retool), and durene (49.2 mg, 0. 366 mmol) in 25 mL of diglyme was stirred at reflux for 48 hours. The conversion of methyl 4-cyanobenzoate was 11.5%, and methyl 4-(aminocarbonyl)benzoate was identified by GC-MS as the only amide product. Acetonitrile is also formed.

Example 5

A solution of acetamide (29.5 mg, 0.50 mmol), p-toluonitrile (58.5 mg, 0.50 mmol), and PdCl$_2$ (5.85 mg, 0.033 mmol) in 1 mL of THF-d$_8$ was heated to 55° C. overnight. The 1H NMR spectrum of the product mixture showed the presence of a mixture of acetamide, p-toluonitrile, p-toluamide, and acetonitrile.

Example 6

A solution of benzamide (60.5 mg, 0.50 mmol), p-toluonitrile (59.3 μL, 0.50 mmol), and PdCl$_2$ (5.85 mg, 0.033 mmol) in 1 mL of 1,4-dioxane-d$_8$ was heated to 90° C. for 8 hours. The $^1$H NMR spectrum of the product mixture showed the presence of a mixture of benzamide, benzonitrile, p-toluonitrile, and p-toluamide. Gas chromatography of the product mixture showed that conversion of p-toluonitrile and yield of p-toluamide were both approximately 5%. Benzonitrile was also formed.

Example 7

A solution of acetonitrile (26 μL, 0. 50 mmol), p-toluamide (67.0 mg, 0.50 mmol), and PdCl$_2$ (7.7 mg, 0.043 mmol) in 1 mL of 1,4-dioxane-d$_8$ was heated to 90° C. for several hours. The $^1$H NMR spectrum of the product mixture showed the presence of a mixture of acetonitrile, acetamide, p-toluamide, and p-toluonitrile.

Example 8

A solution of acetonitrile (26 μL, 20.4 mg, 0.50 mmol), propionamide (35.2 mg, 0.48 mmol), and PdCl$_2$ (6.0 mg, 0.034 mmol) in 1 mL of THF-d$_8$ was heated to 65° C. for several hours. The $^1$H NMR spectrum of the product mixture showed the presence of acetonitrile, acetamide, propionamide, and propionitrile.

Example 9

A solution of acetonitrile (26 μL, 20.4 mg, 0.50 mmol), trimethylacetamide (51.6 mg, 0.5 mmol), and PdCl$_2$ (5.mg, 0.029 mmol) in 1 mL of THF-d$_8$ was heated to 65° C. for 16 hours. Analysis of the product mixture by $^1$H NMR showed that both trimethylacetonitrile and acetamide were formed.

Example 10

A solution of acetonitrile (13 μL, 10.2 mg, 0.25 mmol), isobutyramide (21.0 mg, 0.24 mmol), and PdCl$_2$ (3.0 mg, 0.017 mmol) in 1 mL of THF-d$_8$ was heated to 60° C. for 16 hours. Analysis of the product mixture by $^1$H NMR showed that both isobutyronitrile and acetamide were formed.

Control Example A

A solution of acetamide (29.5 mg, 0.50 mmol) and PdCl$_2$ (5.85 mg, 0.033 mmol) in 1,4-dioxane-d$_8$ was heated to 90° C. for several hours. No apparent reaction took place.

Example 11

To a 250 mL round bottom flask is added 100 mmol of methyl cyanoacetate, 250 mmol of furanamide formed from hydration of furanonitrile, 5 mmol of PdCl$_2$, and 100 mL of THF solvent. The reaction is heated to reflux, forming a slightly colored homogenous solution. Methylacetoacetamide formed is separated by sublimation, leaving behind furanonitrile also formed in the reaction.

Example 12

A solution of acetamide (29.5 mg, 0.50 mmol), acetonitrile-d$_3$ (21.9 mg, 0.50 mmol), and PdCl$_2$ (6.8 mg, 0.038 mmol) in 1,4-dioxane-d$_8$ was heated to 90° C. for several hours. The $^1$H NMR spectrum of the product mixture showed the presence of acetamide and acetonitrile in approximately 55/45 ratio, indicating a conversion of each reactant of about 45 percent. 0.56 mmols of acetamide, 1 mL of acetonitrile-d3, and 0.536 mmols of durene (internal standard) are placed in a 5 mm NMR tube and heated to 70° C. Acetonitrile-d$_3$ serves both as solvent and acetonitrile reactant. After being heated for 16 hours at 70° C., the sample is analyzed by a Bruker 200 spectrometer. No catalyst was used and no product was formed.

Example 13

A solution of acetamide (236 mg, 4.0 mmol), acrylonitrile (0.236 mL, 190 mg, 3.58 mmol), and PdCl$_2$ (709.2 mg, 4.0 mmol) in 5 mL of 1,4-dioxane-d$_8$ was heated to 75° C. for several hours. The $^{13}$C NMR spectrum of the product mixture showed the presence of acetamide, acetonitrile, acrylonitrile, and acrylamide.

Example 14

A solution of adiponitrile (11.36 μL, 10.8 mg, 0.10 mmol), acetamide (30 mg, 0.51 mmol), and PdCl$_2$ (17.7 mg, 0.10 mmol) in 1,4-dioxane-d$_8$ was heated to 70° C. overnight. A white precipitate was collected and identified as adipamide by $^1$H NMR and IR spectrometry. Acetonitrile was also formed.

Example 15

A solution of acetamide (29.6 mg, 0.50 mmol), acetonitrile-d$_3$ (1 mL), and PdBr$_2$ (6.3 mg, 0.024 mmol) was heated overnight at 80° C. Conversion of acetamide was 83% and yield of acetonitrile was 74%, as determined by $^1$H NMR spectrometry.

Example 16

A solution of acetamide (29.6 mg, 0.50 mmol), acetonitrile-d$_3$ (1 mL), and PtBr$_2$ (8.1 mg, 0.023 mmol) was heated overnight at 80° C. Conversion of acetamide and yield of acetonitrile were 60%, as determined by $^1$H NMR spectrometry.

Example 17

A solution of trans-3-pentenamide (10.5 mg, 0.106 mmol) and PdBr$_2$ (7.9 mg, 0.030 mmol) in 1 mL of acetonitrile-d$_3$ was heated at 80° C. for 5 days. The $^1$H NMR spectrum of the product mixture showed the presence of cis-3-pentenamide, trans-3-pentenamide, 4-pentenamide, 2-pentenamide, and 3-pentenenitrile. Acetamide-d$_3$ was also formed.

A solution of trans-3-pentenamide (10.0 mg, 0.10 mmol) in 1 mL of acetonitrile-d$_3$ was heated at 80° C. for 21 hours. No catalyst was added. The $^1$H NMR spectrum of the product solution showed no conversion or isomerization of the trans-3-pentenamide in the absence of catalyst.

Example 18

A solution of formamide (0.5047 g, 11.2 retool), PdBr$_2$ (0.165 g, 0.62 mmol) in 25 mL of benzonitrile was stirred at reflux for 16 hours. At the end of this time, it was found that 0.29 mmol of HCN was produced. Benzamide was also produced.

Example 19

A solution of 3-methoxypropionitrile (182 μL, 2.0 mmol), acetamide (496 mg, 10.1 mmol), and PdCl$_2$ (17.7 mg, 0.10 mmol) in 10 mL of trimethylacetonitrile was heated to reflux for 48 hours. GC-MS of the product solution showed that 3-methoxypropionamide and trimethylacetamide formed. Acetonitrile was also formed.

Example 20

A mixture of acetamide (693.8 mg, 11.7 mmol), p-toluonitrile (58 μL, 56.9 mg, 0.486 mmol), and PdCl$_2$ (5.9 mg, 0.033 mmol) was heated for 16 hours at 100° C. The acetamide served as both solvent and reactant. All the reaction components were soluble in the acetamide above 80° C. $^1$H NMR analysis of the product mixture showed complete conversion of p-toluonitrile to p-toluamide and that acetonitrile was formed.

Example 21

A solution of benzamide (72.9 mg, 0.602 mmol), p-toluonitrile (55.5 mg, 0.474 mmol), durene (13.2 mg, 0.098 mmol, GC internal standard), and PdCl$_2$ (5.7 mg, 0.032 mmol) in 25 mL 1,4-dioxane was heated to reflux for 24 hours. GC analysis of the product solution showed conversion of benzamide to benzonitrile and of p-toluonitrile to p-toluamide was approximately 15%, with >90% material balance.

Example 22

Acetamide (30.1 mg, 0.510 mmol) and 0.8253 g of a stock solution of PdCl$_2$ in acetonitrile-d$_3$ was placed in a 5 mL NMR tube. The PdCl$_2$/acetonitrile-d$_3$ stock solution was prepared by dissolving 108.4 mg PdCl$_2$ (0.611 mmol) in enough acetonitrile-d$_3$ to make 25 mL of solution. The NMR tube was placed in the heated probe of a Nicolet 200 MHz NMR spectrometer and maintained at 70° C. for 4 hours. After 4 hours 13% conversion of acetamide to acetonitrile was recorded, with material balance of >90%. Deuterated acetamide was also formed.

Example 23

A solution of acetamide (30.7 mg, 0.520 mmol), di-t-butylpyridine (10.9 mg, 0.0570 mmol), and PdCl$_2$ (4.3 mg, 0.024 mmol) in 1.0 mL of acetonitrile-d$_3$ was placed in a 5 mL NMR tube. The tube was placed in the heated probe of the Nicolet 200 MHz NMR spectrometer and maintained at 70° C. for 8 hours. $^1$H NMR spectra were recoreded every two hours. 68% conversion of acetamide to acetonitrile was measured after 4 hours, showing the increase in reaction rate in the presence of di-t-butylpyridine. 80% conversion of acetamide to acetonitrile was observed after 8 hours, with material balance of >90%. Deuterated acetamide was also formed. The sterically hindered, non-nucleophilic amine, di-t-butylpyridine, accelerated the reaction.

Example. 24

A solution of adipamide (10 mmol) and PdCl$_2$ (0.5 mmol) in 150 mL of acetonitrile is heated to reflux. GC analysis of the product solution reveals the presence of adiponitrile. Acetamide is also formed.

Example 25

To a 250 mL three-neck flask fitted with an efficient stirrer, gas inlet tube, and reflux condenser connected to an aqueous base purge trap are added acetamide (10 mmol), PdCl$_2$ (0.5 mmol), and 100 mL of 1,4-dioxane. The reaction mixture is heated to reflux with stirring as HCN is bubbled through the solution. GC analysis reveals the presence of formamide and acetonitrile in the product solution.

Control Example B

A solution of PdBr$_2$ (7.5 mg, 0.028 mmol) and durene (5.9 mg, 0.044 mmol, internal standard) in acetonitrile (0.7297 g, 17.77 mmol) was heated to reflux for 25 hours. At the end of this period, no measurable reaction occurred as determined by GC.

As will be evident to those skilled in the art, various modifications of this invention can be made or followed in the light of the foregoing disclosure and discussion without departing from the spirit and scope of the disclosure or from the scope of the claims.

We claim:

1. A process which comprises contacting and catalytically reacting under essentially anhydrous conditions in the liquid phase an amide with a nitrile according to the equation:

$$RCONH_2 + R^1CN \rightleftharpoons RCN + R^1CONH_2$$

where R and R$^1$ are not the same and are each selected from
(1) H, hydrocarbyl, a hydrocarbyl group substituted with: one or more of F, Cl, Br, I, amido, cyano, formyl, hydrocarbylcarbonyl, hydrocarbyloxy, hydrocarbyloxycarbonyl, hydrocarbylcarbonyloxy and dihydrocarbylamino, and
(2) any of group (1) where one or more H atoms are substituted by a deuterium atom, said contacting and reaction being effected in the presence of a catalyst with the formula

$$M_mX_aL_b$$

where M is selected from Pd and Pt, X contains zero to 10 C atoms, is selected from halogen, H, O, —CO, acyloxy, trihaloacetyloxy, hydroxy, dialkylamino, thio, thioacyl, nitro, tetraalkylboron and tetraalkylaluminum;
where m is 1 or 2, a is zero, 2 or 4, and b is 0, 1, 2, 3, 4, or 6; when m=1 and a=zero, b is 2, 3 or 4; when m is 1 and a is 2, b is zero or an integer from 1 to 4; when m is 1 and a is 4, b is 4 or 6; when m is 2, a+b are a total of 6;
where L has the formula $TR^2{}_n$, where T is selected from B, N, P, Bi, Al, As, Sb, Li, Na, K, Rb and Cs; each $R^2$ is the same or different, contains zero to 10 C atoms and is independently selected from H, halogen, nitro, trihalomethyl, acyl, acyloxy, acylthio, hydrocarbyl, hydrocarbyloxy and dihydrocarbylamino; and if T is alkali metal, n is zero; if T is not alkali metal, n is 3 or 4;

with the proviso that the catalyst can optionally additionally contain as a modifier a compound $ZR^2{}_c$ where Z is selected from B, N, P, Bi, Al, As and Sb; $R^2$ is as before defined and c is a number selected to satisfy the valence requirements of Z.

* * * * *